United States Patent
Wei et al.

(10) Patent No.: US 7,026,118 B1
(45) Date of Patent: Apr. 11, 2006

(54) PHARMACEUTICAL COMPOSITION CONTAINING CALCINEURIN B SUBUNIT

(75) Inventors: Qun Wei, Beijing (CN); Mingshan Yan, Beijing (CN); Qinshan Gao, Beijing (CN); Guohua Jiang, Beijing (CN); Mulan Lian, Beijing (CN); Yan Chen, Beijing (CN)

(73) Assignee: Beijing Normal University, Beijing (CN)

( * ) Notice: Subject to any disclaimer, the term of this patent is extended or adjusted under 35 U.S.C. 154(b) by 0 days.

(21) Appl. No.: 09/763,720

(22) PCT Filed: Aug. 29, 1999

(86) PCT No.: PCT/CN99/00126

§ 371 (c)(1),
(2), (4) Date: Apr. 30, 2001

(87) PCT Pub. No.: WO00/12120

PCT Pub. Date: Mar. 9, 2000

(30) Foreign Application Priority Data

Aug. 26, 1998 (CN) .............................. 98117642 A

(51) Int. Cl.
*A01N 37/18* (2006.01)
*A61K 38/00* (2006.01)

(52) U.S. Cl. ................... 435/6; 514/2; 534/6
(58) Field of Classification Search ............... 530/350; 514/2; 435/6
See application file for complete search history.

(56) References Cited

U.S. PATENT DOCUMENTS 6,093,565 A * 7/2000 Hillman et al. .......... 435/252.3

OTHER PUBLICATIONS

Aitken et al. (Eur. J. Biochem. 1984, 139; 663-671).*
Wei et al. (Drug Deveopment 2002; 56: 40-43).*
Rusnak et al. (Physiological Review 2000; 80; 4).*
Klee, C. B. et al., The calmodulin regulated protein phosphatase molecular aspects of cellular regulation, 1988, vol. 5, p225.
Kissinger, C. R. et al., Nature, 1995, 378; 641.
Griffith, J. P. et al., Cell, 1995, 82: 507.
Perrino, B.A. et al., J.B.C., 1996, 270: 340.
Klee, C. B. et al., Adv. Enzymol, 1987, 61: 149.
Wang, M.G. et al., Cytogenet. Cell Genet., 1996, 72: 236.
Shibasaki, F. et al., Nature, 1996, 382: 370.
Li, W. et al., J.B.C., 1993, 268: 14040.
Milan D., et al., Cell, 1994, 79: 437.
Kawamura A., et al., J.B.C. 1995, 270: 15463.

* cited by examiner

*Primary Examiner*—Jeffrey Siew
*Assistant Examiner*—Brandon Fetterolf
(74) *Attorney, Agent, or Firm*—Gehrke & Associates, S.C.; Lisa M. Gehrke

(57) ABSTRACT

The present invention provides a pharmaceutical composition for treatment of mammal disease by regulating the immune system, which contains CaN B subunit and/or its functional derivant in effective amount for treating the disease.

3 Claims, No Drawings

SEQUENCE LISTING

<160> NUMBER OF SEQ ID NOS: 3

<210> SEQ ID NO 1
<211> LENGTH: 169
<212> TYPE: PRT
<213> ORGANISM: Homo sapiens

<400> SEQUENCE: 1

Gly Asn Glu Ala Ser Tyr Pro Leu Glu Met Cys Ser His Phe Asp Ala
1               5                   10                  15

Asp Glu Ile Lys Arg Leu Gly Lys Arg Phe Lys Lys Leu Asp Leu Asp
                20                  25                  30

Asn Ser Gly Ser Leu Ser Val Glu Glu Phe Met Ser Leu Pro Glu Leu
            35                  40                  45

Gln Gln Asn Pro Leu Val Gln Arg Val Ile Asp Ile Phe Asp Thr Asp
        50                  55                  60

Gly Asn Gly Glu Val Asp Phe Lys Glu Phe Ile Glu Gly Val Ser Gln
65                  70                  75                  80

Phe Ser Val Lys Gly Asp Lys Glu Gln Lys Leu Arg Phe Ala Phe Arg
                85                  90                  95

Ile Tyr Asp Met Asp Lys Asp Gly Tyr Ile Ser Asn Gly Glu Leu Phe
                100                 105                 110

Gln Val Leu Lys Met Met Val Gly Asn Asn Leu Lys Asp Thr Gln Leu
            115                 120                 125

Gln Gln Ile Val Asp Lys Thr Ile Ile Asn Ala Asp Lys Asp Gly Asp

-continued

```
            130                 135                 140
Gly Arg Ile Ser Phe Glu Glu Phe Cys Ala Val Val Gly Gly Leu Asp
145                 150                 155                 160

Ile His Lys Lys Met Val Val Asp Val
                165

<210> SEQ ID NO 2
<211> LENGTH: 26
<212> TYPE: DNA
<213> ORGANISM: Artificial Sequence
<220> FEATURE:
<223> OTHER INFORMATION: primer

<400> SEQUENCE: 2
ccgccatatg ggaaatgagg cgagtt                                    26

<210> SEQ ID NO 3
<211> LENGTH: 27
<212> TYPE: DNA
<213> ORGANISM: Artificial Sequence
<220> FEATURE:
<223> OTHER INFORMATION: primer

<400> SEQUENCE: 3
cgcgggatcc tcacacatct accacca                                   27
```

PHARMACEUTICAL COMPOSITION CONTAINING CALCINEURIN B SUBUNIT

This application is a 371 of PCT/CN99/00126, filed Aug. 29, 1999 and which claims priority to under 35 U.S.C. 119 of Chinese application serial number 98117642.9, filed on Aug. 26, 1998, the content of each of which are fully incorporated herein by reference.

TECHNICAL FIELD

The present invention relates to a medicament containing Calcineurin subunit B.

PRIOR ART

Calcineurin (CaN) is the only calcium and calmodulin (CaM)-dependent protein phosphatase as far as we know. It was first discovered and purified from mammal brains in the late 1970s and early 1980s. It was later found that calcineurin also occurs in the non-neural tissues of rabbits and in some cancer cells. CaN, with molecular weight of 80 KD, is a heterodimer consisting of a 61 KD catalytic subunit A and a 19 KD regulatory subunit B (Klee, C. B. et al., The calmodulin regulated protein phosphatase molecular aspects of cellular regulation, 1988, Vol 5, p225).

The subunit A of CaN is the catalytic and regulatory core of the holoenzyme. It includes at least four domains, a metal ions-binding domain (or catalytic domain), a calcineurin B-binding domain, a regulatory effector calmodulin-binding domain and a autoinhibitory domain. The catalytic domain is located on subunit A, which is supported by the fact that subunit A still have the activity of protein phosphatase even if subunits A and B are separated apart. CaN is a serine/threonine protein phosphatase. It was named as protein phosphatase 2B. The amino acid sequence of catalytic subunit A is highly homologuous to other members of the phosphatase family, especially phosphatase 1 and 2A. This homology mainly lies in their catalytic domains, thus their catalytic mechanisms are very similar from each other. Because each phosphatase has special regulatory domain and subunit, thus they are different in structure and function. CaN subunit A differs from other phosphatases in that it have an additional fragment of 170 amino acids containing a subunit B-binding domain, a CaM-binding domain and an autoinhibitory domain in the C-terminus of CaN subunit A, each of them is involved in the regulation of the phosphatase activity of CaN.

The human CaN subunit B is composed of 169 amino acids, and is a member of the calcium-binding protein family. Its primary structure is quite similar to CaM, and troponin C. For example, CaN subunit B and CaM exhibit 31%–35% identity over the amino acid sequence. Both CaN B and CaM contain four putative EF hand $Ca^{2+}$-binding sites. Their secondary structures are also quite similar, each protein contains two globular two $Ca^{2+}$-bingding domains, and two central α-helix which connects the two domains. But there still are some differences between CaN B and CaM. The two calcium-binding domains of CaM are arranged on opposite sides of the central α-helix. However, for CaN B, the two calcium-binding EF-hand domains connect via an α-helix that kinked at Gly-85, and they are arranged linearly along the BBH (subunit B binding helix) of CaN A, together with the amphipathic C-terminal strand, form a hydrophobic groove into which the top half of BBH is embedded. This hydrophobic groove forms the structural basis connecting A and B subunits (Kissinger, C R et al. Nature, 1995, 378: 641; Griffith, J P et al., Cell, 1995, 82: 507). Another difference between CaM and CaN B is that a 14 carbon myristatic acid is connected with the N-terminal glycine residue of CaN B. CaN subunit B does not possess the catalytic activity of protein phosphatase, however, it is highly specific for enzyme activity of the CaN. Although CaN B and CaM function coordinately in the catalytic regulation of CaN A, they play different roles and are irreplaceable between each other. It is known that $Ca^{2+}$ binding to CaN subunit B regulates enzyme activity by lowering Km of the catalytic subunit A for substrate (Perrino, B A et al., J.B.C., 1996, 270: 340).

CaN is a conserved protein, has very broad tissue distribution in eucaryotes. It was found in various tissues including the brain homogenate of human, rat, mouse, pig, frog, fish, and chicken, and non-neural tissues of human and rabbit. CaN B has been found in gastrula crude extract of *Drosophila melanogaster*, but no CaN subunit A was found. A CaM regulated protein phosphatase, found in sea urchin, have the same subunit composition as CaN, and the peptide map of its small subunit is similar to that of CaN B. But the peptide map of its large subunit is different from that of CaN A (Klee, C B et al., Adv. Enzymol., 1987, 61: 149). This indicates that subunit B is more conserved compared with subunit A.

In the studies we have carried out, an anti-mouse CaN antibody was used to detect CaN from human brains and various tumors. The results shows subunit B is present in some tumors such as human brain colloid tumor and meninges tumor in large quantity, but subunit A is hardly detectable. In mouse liver cancer ascites, both A and B subunits can be detected, and there are more subunit B than A (Qun Wei, et al. Chinese Journal of Biochemistry, 1993, 9: 240). Ongoing studies of the functions of CaN in cancer tissues should be furthered to more deeply understand the disease mechanisms.

Several CaN cDNA clones have been obtained from the brain tissue gene libraries of human, rat, mouse, and rabbit. In eucaryotic organisms, CaN A is encoded by three genes, named as CaN Aα, β, and γ, respectively. The so-called Aα and Aβ genes were located on human chromosomes 4 and 10(10q21–q22), respectively. However, CaN B is highly conserved, only one gene was found till now, which is located on chromosome 2(2p16–p15) (Wang, M G et al., Cytogenet. Cell Genet., 1996, 72: 236).

Although the mammal CaN subunit A and B cDNAs were obtained in the late 1980s, how to express them in *E. coli* in high yield and in active form remains a problem. It has been reported that they can be expressed in insect cells or other cells. Some expressed proteins are in the form of inclusion bodies, thus it was quite difficult to have them extracted and purified. In some reports subunits A and B are coexpressed. We have succeeded in expression of A and B, respectively, in *E. coli*. To our surprise, the expression level of subunit B is high enough to make this system useful for production of the enzyme in an amount sufficient for isolation, and the purification method was unbelievably simple. Furthermore, the high homology of human, rat, and bovine CaN subunit Bs gives a solid base for pharmaceutical use of this subunit.

CaN has many important biological functions. As the only calcium, calmodulin-dependent protein phosphatase known up to now, it plays an important role in calcium signal transduction and reversible substrate phosphorylation involved in many physiological, pathological processes. Because of its high content in brains, CaN is related to many functions of the brain. More and more attention is being focused on its relation to the ability of learning, memory, and Alzheimer's Disease. Most recently, CaN was found to be the key factor in T-cell activation.

CaN is the key enzyme in T cell activation, which is supported by the fact that it is the common target of different immunosuppressant drugs, such as FK506, CsA, etc. The role of CaN in T cell activation is being elucidated. It was reported that, NF-AT is the substrate of CaN. It was also proved that CaN functions in the way by translocating from cytoplasm to nucleus through binding to NF-AT (Shibasaki, F, et al., Nature, 1996, 382: 370). The mechanism of the function of CaN in nucleus has been elucidated. It binds to the promoter region of IL-2 gene, which directs the expression of the IL-2 gene. After the IL-2 is excreted out of cells, it binds to the receptor on T cell surface, effecting the proliferation of the T cells.

Most researches which have been carried out directing the biologically function of CaN were focused on its protein phosphatase characteristic, and most experiments were conducted in the presence of both CaN subunits A and B. A few were carried out only in the presence of CaN A or its mutants. There are several reports about the characterization of the biological function of CaN B, especially about the important function of CaN B in the combination of CaN with immunosupressant FK506, CsA and their respective immunophilin FKBP-12, cyclophilin (Li, W. et al., J.B.C., 1993, 268: 14040; Milan D, et al., Cell, 1994, 79: 437; Kawamura A. et al., J.B.C. 1995, 270: 15463; Griffith, J P, et al. Cell, 1995, 82: 507), however, it is believed that this process needs the presence of CaN A. Up to now, there are no reports on the physiological effects by injecting CaN B alone into the body, and there are no reports on CaN B being an anticancer drug and a biological reaction regulator.

The immune state of the body relates closely to the occurrence and development of cancers. Early in 1970, Burnet put forward the theory of immune surveillance, which believes that the immune function evolves as the mechanism of preventing mutation of normal cells to cancer cells, and the mammals recognize and annihilate the cancerized cells primarily through T lymphocytes. In recent years, there are a lot of notable progresses on the research of antigenicity of human and animal cancers, anti-cancer effector cells, and how cancer cells to evade immune surveillance of the body. It is now understood that, except for T cells among the effector cells possessing immune surveillance function, some other cells also participate in this process. The anticancer immune function recognizes not only the cancer related antigens but also the other abnormal phenomenon relating to cancer cells. It is also believed that, cancer is prone to occur as the immune function is injured. Furthermore, recent research indicated that the damage of the immune function is mainly due to the loss of normal immune regulation.

The development of immunology elucidated that, for all the animals including human beings, the immune function is regulated by a rather complicated and quite accurate regulatory system which is called immune regulation complex. Except for the neural and endocrine system, the entire complex can be divided into two parts: the upward regulation, in which regulatory cells and its secretion products strengthen the immune response; and the downward regulation, in which regulatory cells and its secretion products weaken the immune response. Normally, the immune system reacts exactly to all kinds of stimulation from inside and outside of the body by way of the upper and nether regulations. So the immune system functions at a homeostasis state. Due to some causes like cancer growth, senescence, virus infection, chronic infection, radiological therapy, and the like, the homeostasis is often disturbed or destroyed, so the immune function is greatly weakened. If the immune function is positively regulated (upward regulation), it will be in favor of the control and amelioration of the diseases. The immune regulatory drug exerts the therapeutic function just by regulating the immune function of the body from different aspects. Wherein the immune regulatory substance derived from organism itself is named as Biological Reaction Regulator.

The result of a number of studies showed that, CaN is the key enzyme in T cell activation and also the common in vivo target enzyme of immunosupressant FK506 and CsA. CaN B plays an important role in the binding of immunosuppressant, immunophilin with CaN. CaN B is a highly conserved protein. It has the same amino acid sequence in human, bovine, and rat.

SUMMARY OF THE INVENTION

It is one object of the present invention to provide the use of CaN subunit B for the manufacture of medicament for the treatment of mammal diseases by regulating the immune system.

It is another object of the present invention to provide a composition for the treatment of mammal diseases containing effective amount of CaN subunit B or its derivatives possessing CaN B function.

DETAILED DESCRIPTION OF THE INVENTION

The present invention provides the use of CaN subunit B for the manufacture of medicament for the treatment of mammal diseases by regulating the immune system.

The present invention also provides a composition for the treatment of mammal diseases, which containing effective amount of CaN subunit B or its derivatives possessing CaN B function.

The composition of the present invention may contain a pharmaceutically acceptable carrier or excipient besides CaN subunit B or its derivatives possessing CaN B function.

The composition of the present invention can be used in the treatment of mammal diseases that can be treated by regulating the mammal immune response, such as cancer, chronic virus infection, senescence, immune depression caused by radiotherapy treatment, and other diseases caused by the disorder of immune function.

The mammals that can be treated with the composition of the present invention can be any mammal, such as human, mouse. The effective amount for treatment of cancer in mouse is 10–200 μg/day/mouse (for human clinical the effective amount is 100–2000 μg/kg body weight/day), which can be administered by one dosage or several dosages per day. There are no special restrictions on the route of administration, which may be by vein, or by abdominal cavity. It is preferred to administer successively for many days, for example 5 to 50 days.

The amino acid sequence of the above mentioned CaN subunit B, SEQ ID NO: 1, is as follows:

1       GNEASYPLEMCSHFDA-
    DEIKRLGKRFKKLDLIDNSGSLS-
    VEEFMSLPELQQ
51              NPLVQRVIDIFDTDGNGEVDFKE-
    FIEGVSQFSVKGDKEQKLRFAFRIYDM
101                  DKDGYISNGELFQVLKM-
    MVGNNLKDTQLQQIVDKTIINADKDGDGRISFE
151 EFCAVVGGLDIHKKMVVDV

For CaN B derivatives obtained by the addition, deletion, substitution of one or more amino acids in the above mentioned sequence, or the functional derivatives obtained by chemical modification of the side chains of one or more of the amino acids, can also be used in the composition of the present invention, so long as it remains the biological activity of CaN subunit B.

In vitro experiments demonstrated that, CaN B functions by directly acting on spleen lymphocytes in rats, making them to proliferate 4–7 times. CaN B and mitogen Con.A obviously act synergistically in the stimulation to lymphocytes. 62.5 μg of CaN B can reverse 88% of the immune inhibitory effect of cortisone. In vivo experiments in mouse also indicated that CaN subunit B can accelerate the augmentation of spleen which is an important immune organ. This result proved that CaN subunit B is an excellent immune upward regulation agent or an excellent biological response regulator.

The in vivo anticancer effect of CaN subunit B is significant, it can remarkably reduce the ascites of H22 liver cancer mouse, and can prolong the life by 50–83% of the mouse suffering from cancer. With the dosage as above, CaN B can inhibit the tumor growth of S180 solid tumor by more than 57%. The difference is statistically significant compared with the control group.

The acute toxicity experiment showed that the toxicity of CaN B is negligible. No mouse died in 24 hours during the acute toxicity experiment when 4–50 times of the effective dosage was administered.

The present invention is based on the fact that we have expressed CaN subunit B in *E. coli* in high level and purified it efficiently from lysate. We have used CaN B directly or its functional derivatives as a drug in the treatment of disease of mammal.

EXAMPLES

Example 1

CaN subunit B cDNA was obtained from rat brain cDNA library (Perrino B et al., J. Boil. Chem., 1996 270:340). Forward primer, SEQ ID NO:2, was designed as 5'-CCGC-CATATGGGAAATGAGGCGATT-3', reverse primer. SEQ ID NO:3, was designed as 5'-CGCGGGATCCTCACA-CATCTACCACCA-3'. After PCR amplification, the expected CaN B gene cDNA fragment purified from agarose gel and pET21a vector were double-digested with restriction enzymes Nde I and BamHI, ligated with T4 DNA ligase and transformed into BL21(DE3) plysS *E. coli*. The positive clones were kept at 4° C. in LB solid medium containing 50 μg/ml Amp. 1 liter of TM medium containing 50 μg/ml Amp was inoculated with 5–10 ml freshly grown culture. The culture was incubated 5–6 hrs in an air shaker at 37° C., 250 rpm. The cells from the above culture were spun down at 5000×g for 20 minutes at 4° C. After discarding the supernatant, the cell pellet were stored at −20° C.

Example 2

Construction and Expression of CaN Subunit B Splicesome and Mutants

The N- and C-terminal CaN B splicesomes were obtained through PCR amplification using specifically designed primers. Non-N terminal and non-C terminal mutants construction was performed by pAlter mutation plasmid system (Promega). The expression system was the same as wild-type CaN subunit B.

Example 3

The Preparation of CaN Subunit B

1. Breaking Cells: The cell pellet from 1 liter culture was resuspended in 50–100 ml ice-cold cell lysis buffer (20 mM Tris-HCl, pH 7.4, 1 mM EDTA, 0.2 mM PMSF, 1 mM β-mercaptoethanol). The cells were broken by sonication (200 W, 2–3 minutes).

2. Protein extraction and purification: After the cells were broken, the mixture was kept at 100° C. boiling water for 30–40 minutes, the supernatant was obtained by centrifugation at 12,000×g for 20 minutes. The supernatant was CaN subunit B crude extract. The hydrophobic Phenol-Sepharose CL-4B column was used for purification of CaN subunit B. After the column was equilibrated with equilibration buffer (20 mM Tris-HCl, pH 7.4, 0.5 mM $CaCl_2$, 1 mM β-mercaptoethanol), the extract (added 3 mM $CaCl_2$, 1 mM β-mercaptoethanol) was slowly loaded onto the column. No less than 10 bed volumes of the equilibration buffer was required to thoroughly wash the column. After washing, the target protein was eluted from the column using the elution buffer (20 mM Tris-HCl, pH 7.4, 1 mM EDTA, 0.5 mM DTT). About 120 mg electrophoretically pure protein was obtained from 1 liter culture. The purified protein was lyophilized and stored at −20° C.

Example 4

Detection, Identification, Quality Control and Method of Use

1. DNA sequencing: The cDNA contains 507 nucleotides, the sequence of which is the same as the reported CaN subunit B cDNA sequence.

2. Amino acid sequencing: The 10 N-terminal amino acids of CaN B are, SEQ ID NO:4, gneasyplrm. This indicated that expressed protein is the human CaN subunit B protein as reported. Both rat and human have the same amino acid sequence of CaN B.

3. Purity analysis: Over 98%, which is shown by SDS-PAGE.

4. Identification of physical and chemical characteristics: IP=4.8, standard absorbance $\epsilon_{277nm}^{1\%}=3.1$.

5. Concentration analysis: UV-spectrophotometric method.

6. Identification experiment: Positive result in Western Blot using anti-CaN subunit B antibody; UV-spectrum.

7. Biological activity: Activation of CaN subunit A.

8. Characters and Method of use: CaN subunit B is highly soluble in water, the water solution is colorless and quite clear. Soluble in physiological saline or pH-neutral buffer (mannitol can be added), CaN subunit B can be kept at −20° C. for over 2 years.

Example 5

In Vivo Anti-Cancer Experiments of CaN B

1. Prevention Experiment, Life Prolongation Experiment, and Dose Experiment of H22 Liver Ascites Cancer:

Materials and method: BAL B/C mouse, ♂, weight 20±1 g. The mouse of experiment group were injected (i.p.) CaN subunit B 10, 100, or 200 ug/0.2 ml/day/mouse, the mice of control group were injected (i.p.) PBS 0.2 ml/day/mouse. After two days the mice were inoculated $1\times10^6$ H22 ascites cancer cells, and at the same time, CaN B or PBS was injected (totally for 7 days). The living time of each mouse was recorded after inoculation. The life prolongation rate was calculated according to the formula as follows, and the result is shown in Table 1 and 2 below.

$$\text{Life prolongation rate} = \frac{\text{Average living days of experiment group} - \text{Average living days of control group}}{\text{Average living days of control group}} - X\ 100\%$$

TABLE 1

| Groups | Average living days ± SD | Life prolongation rate | t-test |
| --- | --- | --- | --- |
| Control | 19.5 ± 0.76 | | |
| 10 μg CaNB | 24.6 ± 3.35 | 26% | <0.2 |
| 100 μg CaNB | 29.2 ± 1.36 | 50% | <0.001 |

TABLE 2

| Groups | Average living days ± SD | Life prolongation rate | t-test |
| --- | --- | --- | --- |
| Control | 18.75 ± 0.5 | | |
| 200 μg CaNB | 34.25 ± 4.6 | 82.7% | <0.001 |

2. Treatment Experiment of H22 Liver Ascites Cancer, Life Prolongation Experiment:

Materials and method: BAL B/C mouse, ♂, weight 20±1 g, were inoculated (i.p.) with $1 \times 10^7$ H22 ascites cancer cells. The mice were randomly divided into two groups: experiment group, which was injected with CaN subunit B of 200 μg/0.2 ml/day/mouse; control group, which was injected with PBS of 0.2 ml/day/mouse. The living days after inoculation were recorded, and the result is shown in Table 3 below.

TABLE 3

| Groups | Average living days ± SD | Life prolongation rate | t-test |
| --- | --- | --- | --- |
| Control | 19.0 ± 1.6 | | |
| Experiment | 29.0 ± 8.9 | 52.6% | <0.025 |

3. Treatment Experiment of S180 Solid Cancer:

Materials and method: Kunming White mouse, ♂, weight 20±1 g, was inoculated (i.e., at armpit) with $1 \times 10^7$ S180 ascites cancer cells (about 0.2 ml/mouse). The inoculated mice were randomly divided into two groups. After four days (when the tumor was visible), the control group was injected with PBS of 0.2 ml/day/mouse, and the experiment group was injected with CaN subunit B of 100 ug/0.2 ml/day/mouse (totally for 7 days). After 24 hours from the latest injection, the mice were killed and the solid tumor and spleen were removed from the body, and were weighted. The tumor inhibition rate was calculated according to the formula as follows and the result is shown in Table 4 below.

$$\text{Tumor inhibition rate} = \frac{\text{Average tumor weight of control group} - \text{Average tumor weight of control group}}{\text{Average tumor weight of control group}} X\ 100\%$$

TABLE 4

| Groups | Average spleen weight ± SD | Weight increase rate | t-test | Average tumor weight ± SD | Inhibition rate | t-test |
| --- | --- | --- | --- | --- | --- | --- |
| Control | 0.25 ± 0.09 | | | 1.38 ± 0.66 | | |
| Experiment | 0.32 ± 0.08 | 25.5% | <0.1 | 0.59 ± 0.39 | 57.1% | <0.01 |

Example 6

In Vitro Cell Biological Immune Experiments of CaN B

1. The Direct Effect of CaN Subunit B on Rat Spleen Cell Proliferation:

Materials and method: Rat spleen lymphocytes were obtained by using conventional method, then were suspended in 1640 culture medium at a concentration of $5 \times 10^6$ cells/ml. Each well of 96 well plate contained $5 \times 10^5$ cells in 0.2 ml, and CaN subunit B was added at the concentration of 0, 2.5, 12.5, or 62.5 μg/ml. The cells were cultured for 48 hrs at 37° C., 5% $CO_2$. Then $^3$HdR (0.5 μCi/well) was added, and the cells were cultured for 8–16 hrs. The cultured cells were collected onto a glass fiber membrane using multiple-head cell collector. After the membrane was dried, scintillation solution was added, and cpm value was obtained by using a scintillation counter. Then the difference between before and after addition of CaN subunit B was obtained. The difference was showed in the form of proliferation times calculated according to the formula as follows, and the result is shown in Table 5 below.

$$\text{Proliferation Times} = \frac{\text{Average } cpm \text{ value of } CaN\ B \text{ group}}{\text{Average } cpm \text{ value of control group}} \times 100\%$$

TABLE 5

| Dosage | cpm ± SD | Proliferation times | t-test |
| --- | --- | --- | --- |
| 0 (control) | 467 ± 81 | | |
| 2.5 μg CaN subunit B | 375 ± 25 | | |
| 12.5 μg CaN subunit B | 1704 ± 194 | 3.7 | <0.001 |
| 62.5 μg CaN subunit B | 3041 ± 390 | 6.5 | <0.001 |

2. The Synergistic Effect of CaN Subunit B and Con.A in the Proliferation of Rat Spleen Lymphocytes:

The materials and method are the same as that in part 1 of example 6. At the same time of adding CaN subunit B, the immune stimulator Con.A was also added at a concentration of 5 μg/ml. The synergistic effect of CaN subunit B and Con.A in the proliferation of rat spleen lymphocytes was clearly seen from the result as shown in Table 6 below.

TABLE 6

| Dosage | cpm ± SD | Proliferation times | t-test |
|---|---|---|---|
| 0 (control) | 158000 ± 3200 | | |
| 2.5 μg CaN subunit B | 155000 ± 7000 | | |
| 12.5 μg CaN subunit B | 174000 ± 5200 | 10.2% | <0.001 |
| 62.5 μg CaN subunit B | 192000 ± 3600 | 21.8% | <0.001 |

3. The Reverse Effect of CaN Subunit B in the Immune Inhibition of Cortisone:

The materials and method are the same as that in part 1 of example 6. On a 96-well microtiter plate, after the cell culture was added, immune stimulator Con.A was added at a concentration of 5 μg/ml, then cortisone ($10^{-7}$ mM/L) and thereafter CaN B was added. The result of reverse effect of CaN subunit B on the immune inhibition of cortisone was shown in Table 7 below.

TABLE 7

| Dosage | cpm ± SD | Proliferation times | t-test |
|---|---|---|---|
| 0 (control) | 66400 ± 4500 | | |
| 2.5 μg CaN subunit B | 63500 ± 2800 | | |
| 12.5 μg CaN subunit B | 73900 ± 4000 | 19.4% | <0.001 |
| 62.5 μg CaN subunit B | 125000 ± 5100 | 87.9% | <0.001 |

Example 7

Acute Toxicity Experiment of CaN Subunit B on Mouse

Animals: BAL B/C mouse, ♂, weight 20±1 g.
Results:

TABLE 8

| Groups (dosage) | Number of animals | Number of died animals | | |
|---|---|---|---|---|
| | | 0–24 hrs | 24–48 hrs | 48 hrs–1 month |
| 4 times of normal dosage (0.4 mg/0.2ml/mouse) | 4 | 0 | 0 | 0 |
| 20 times of normal dosage (2 mg/0.2 ml/mouse) | 4 | 0 | 0 | 0 |
| 50 times of normal dosage (5 mg/0.2 ml/mouse) | 8 | 0 | 3 | 0 |

---

What is claimed is:

1. A method for treatment of cancer in a mammal comprising administering an effective amount of SEQ ID NO: 1 to the mammal.

2. The method of claim 1, wherein the mammal is human.

3. The method of claim 1, wherein the effective amount is 100–2000 µg/kg body weight/day.

* * * * *